US00PP09311P

United States Patent [19]

Bost

[11] Patent Number: Plant 9,311

[45] Date of Patent: Oct. 3, 1995

[54] HIBISCUS PLANT NAMED 'QUATRO ROJO'

[76] Inventor: Georgia A. Bost, 1209 Pine Chase, Houston, Tex. 77055

[21] Appl. No.: 343,377

[22] Filed: Nov. 22, 1994

[51] Int. Cl.[6] ..... A01H 5/00

[52] U.S. Cl. ..... Plt./67.8

[58] Field of Search ..... Plt./67.8

[56] References Cited

U.S. PATENT DOCUMENTS

P.P. 835 5/1949 Hemming ..... Plt./67.8

P.P. 4,271 6/1978 Darby ..... Plt./67.8

P.P. 5,209 3/1984 Darby ..... Plt./67.8

P.P. 7,608 7/1991 Winter ..... Plt./67.8

*Primary Examiner*—James R. Feyrer

*Attorney, Agent, or Firm*—Martin L. McGregor

[57] ABSTRACT

An herbaceous perennial Hibiscus plant named "Quatro Rojo" having numerous large polypetalous flowers with four zones of rich reds with petals smoothly reflexed, buds of darker red, and giant, well-branched, upright plants with large, 3- to 5-lobed leaves of deep green color.

3 Drawing Sheets

HISTORICAL NOTE

As of October 1994, there are a total of only 18 patents granted for the species Hibiscus in the United States of America. The earliest patented hibiscus plant (U.S. Plant Pat. No. 835), identified in records simply as 'Mallow', was selected from a population having within its genetic background *Hibiscus militaris, H. coccinea* and *H. moscheutos.* This early improved plant was characterized by having smooth, deeply cut leaves, as attaining a shrub height of medium size, of having medium-sized (6–8 inch flowers) with deep red, imbricated flower petals and by being adapted for culture in the temperate zone. Within the remainder, 10 are *H. rosa-sinensis* types developed by Frank Moser; three more are also *H. rosa-sinensis* varieties, developed by Roberta Ludick; and one is a variegated sport of *H. paeoniflorus,* selected by Harold Hillis. All of these varieties are tropical, mostly pan-Pacific species that do not survive unprotected north of USDA Zone 10.

The novel plant invention described herein is of the perennial hibiscus type that is native to the continental United States. There are currently only three patented varieties of this type of hibiscus: "Lady Baltimore" (Darby, U.S. Plant Pat. No. 4,271), "Anne Arundel" (Darby, U.S. Plant Pat. No. 5,209), and "Sweet Caroline" (Winters, U.S. Plant Pat. No. 7,608). All three of these were developed from East Coast populations of the species hibiscus *H. moscheutos, H. moscheutos* spp. *palustris,* and *H. laevis* (formerly *H. militaris*), in various combinations with the SE Gulf Coast species, *H. coccineous.*

BACKGROUND OF THE NEW PLANT

The BOST$_x$® breeding program which produced the nvoel plant invention described herein and named "Quatro Rojo" ("Quatro") extended over a period of some 9 years. QUATRO originated as a seedling selected from progeny of cross pollination between (1) a breeding line derived from crossing the commercially available *Hibiscus moscheutos*× 'Southern Belle' and a Texas species hibiscus *H. laevis* selection "Houston", (2) a breeding line derived from crossing *H. laevis* "Houston" and species hibiscus *H. coccineus,* and (3) a breeding line derived from crossing *H. coccineus* and Hibiscus×"Southern Belle".

Unfortunately, the original tag documenting the pod and pollen parents of the seedling was unreadable at the time the plant was evaluated. The probable parents are BOST$_x$® $F_1$ generation selections "Nathan's Star" and "Georgia Rose". Quatro clearly shows characteristics of all three of the original parent ($P_1$) genomes used to establish this breeding program.

The objective of the breeding program which produced the novel plant of the invention was primarily to develop a plant with the following characteristics:

(a) Large plant of exceptional productivity suitable for cultivation with good form and reliably upright habit.

(b) Decorative foliage of a pleasing shade of green with unique shape and size characteristics not shared by current landscape varieties.

c) Attractive, well-formed, large red flowers that are distinctive for the color and form, that are well-posed on the plant and that remain open for most of the day (two days in cooler weather).

SUMMARY OF THE INVENTION

The present invention comprises a new and distinct cultivar of herbaceous perennial Hibiscus hybrid hereinafter referred to by the cultivar name "Quatro Rojo" (or "Quatro"). QUATRO was a seedling selected by Georgia A. Bost in July 1992 from a seedling population grown in a cultivated area of her nursery, The Village Botanica, Inc. at 7500 Westview Drive, Houston, Tex. She is the owner of the clone and controls all propagations of it. The new plant produced its first flower in the summer of 1992 and, because of the size and brilliant coloring of the flower, its stellar form, its attractive foliage and giant habit, it was selected for reproduction and testing. Asexual propagation of this new plant by cuttings was carried on at The Village Botanica, 7500 Westview Drive, Houston, Tex., in 1993 and at JJL Greenhouse, Inc., 1449 Brittmoore, Houston, Tex., in 1994, under exclusive contract to The Village Botanica, Inc. Observation of the progeny of the original plant has demonstrated that this new variety has fulfilled the objectives and that its distinctive characteristics are firmly fixed and hold true from generation to generation vegatatively propagated from the original clone.

The new cultivar is of value for its floral display, produced from late May until late November (or frost), depending upon USDA zone, environmental conditions and culture;

and for the landscape value of the entire plant; and as a source of plant materials for commerical products.

DETAILED DESCRIPTION OF THE DRAWINGS

Figure 1:
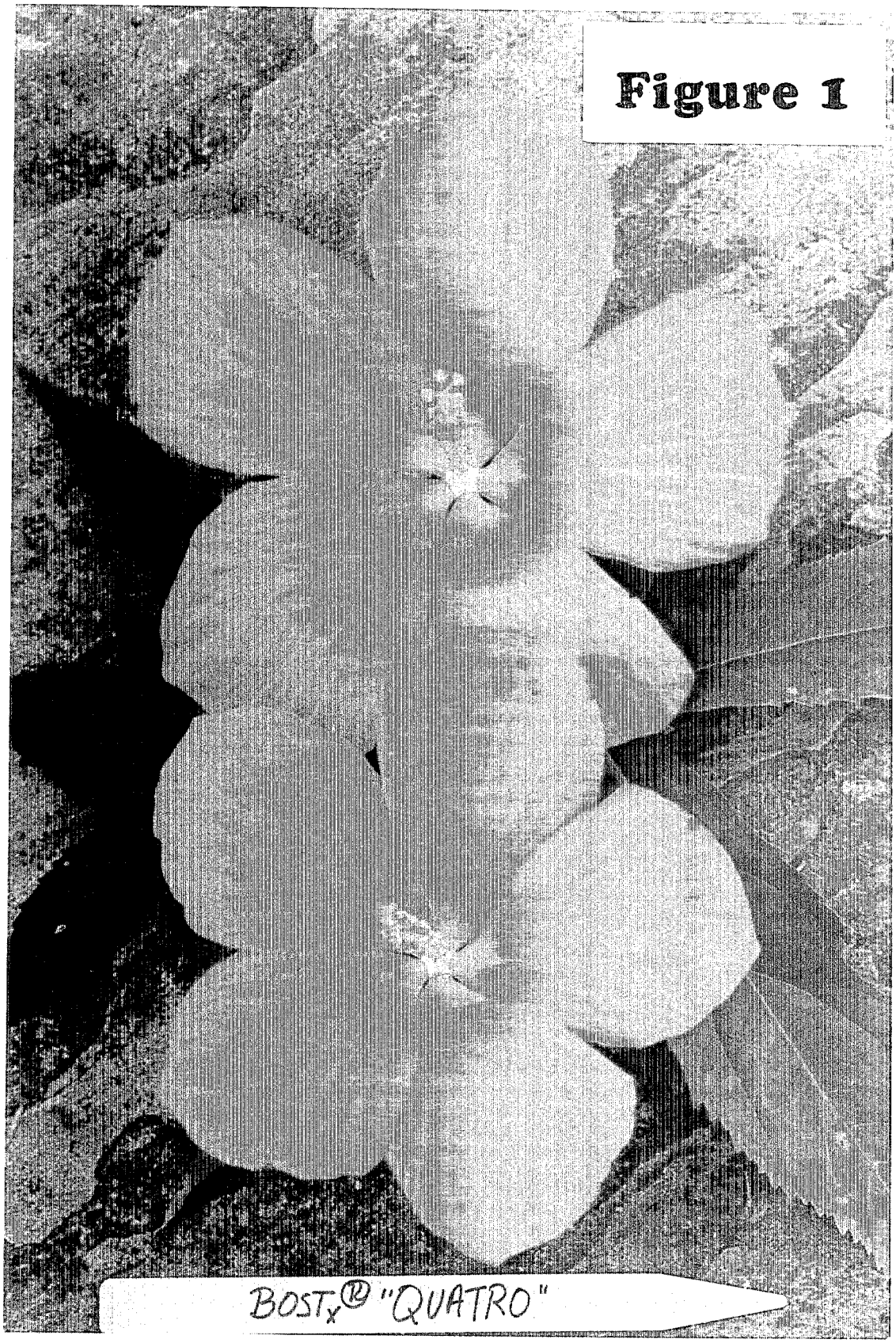
Figure 2:
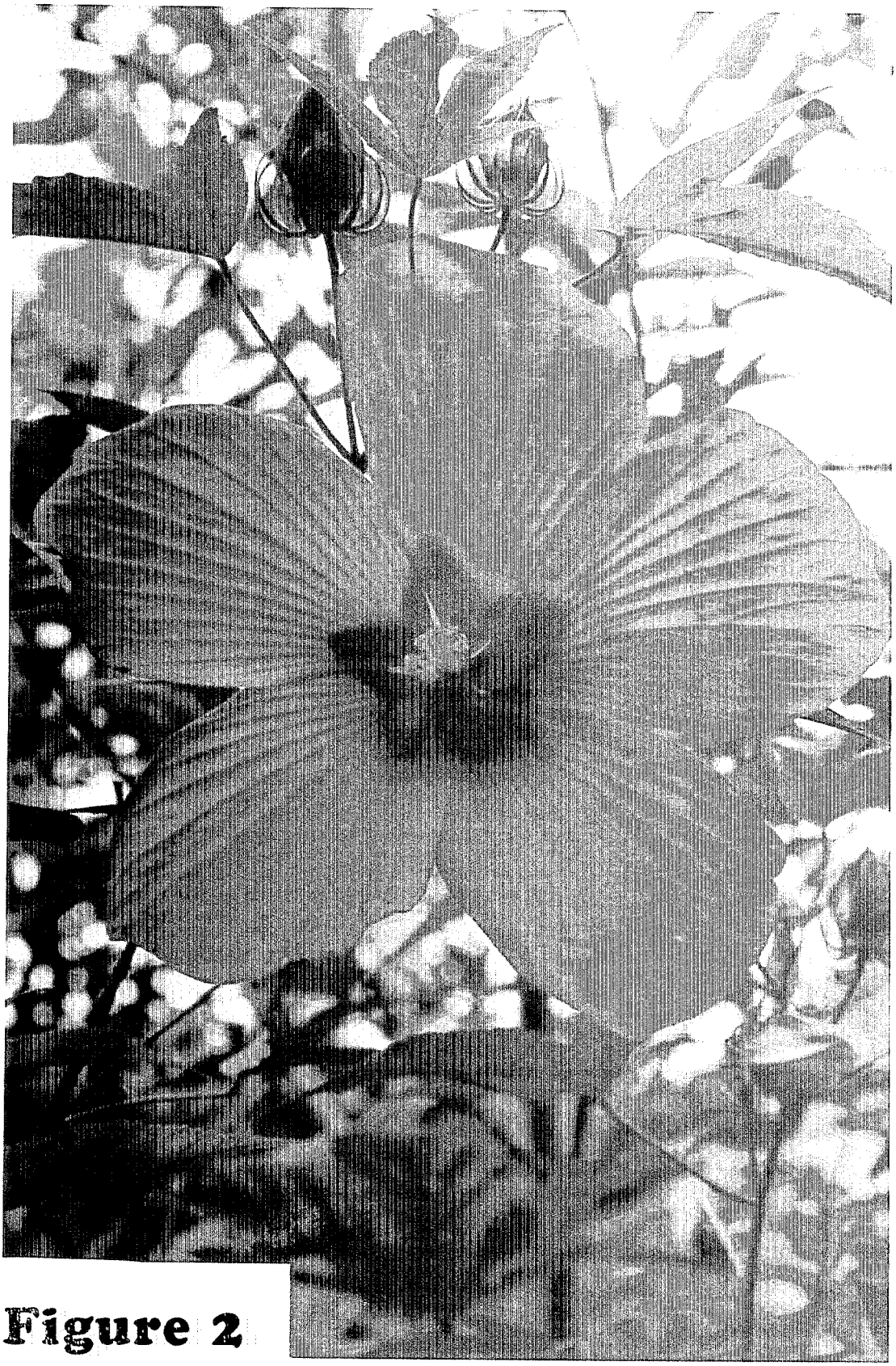
Figure 3:
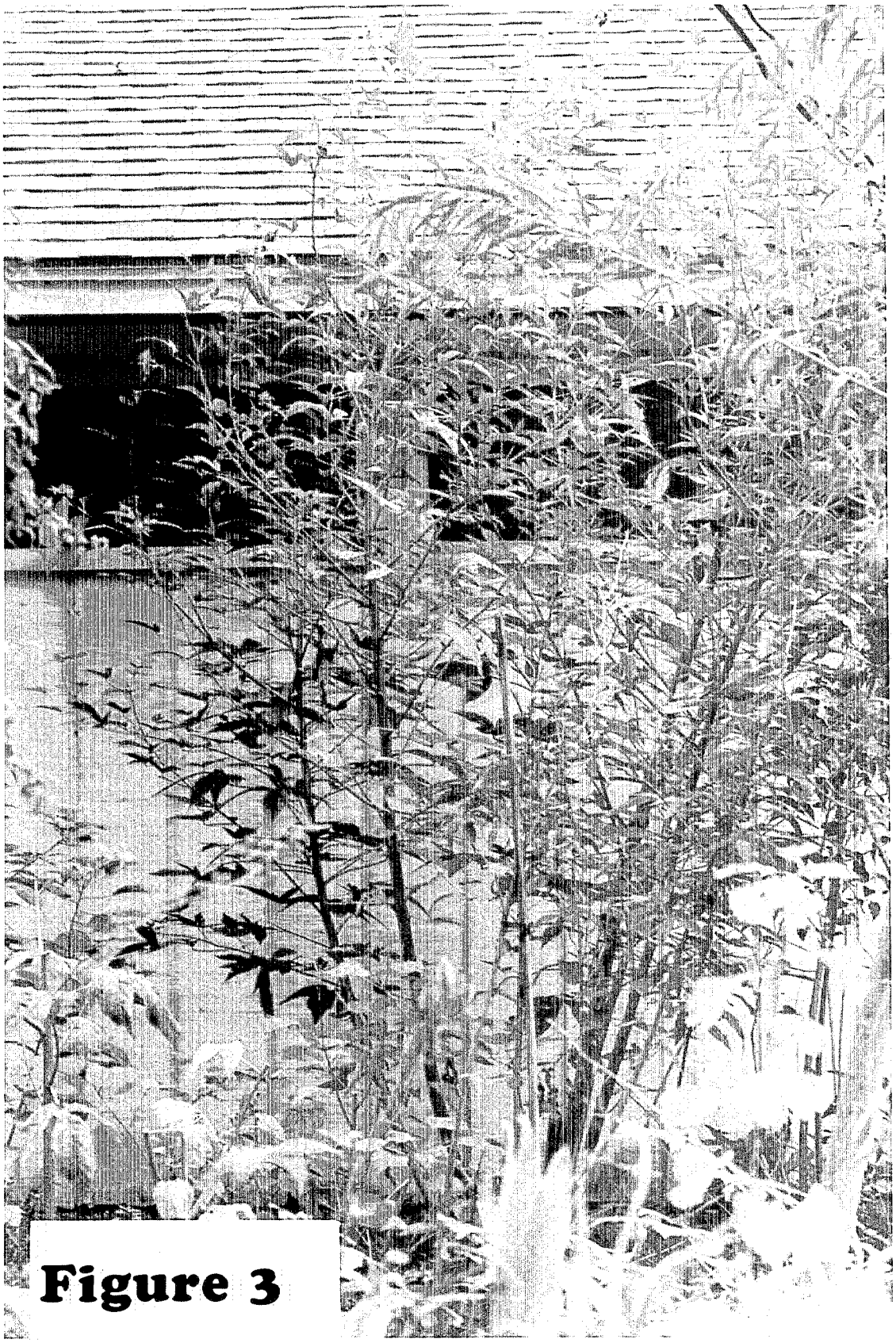

This new variety of perennial hibiscus is illustrated by the accompanying full color photographic drawings which show:

FIG. 1 two fully opened flowers and some typical leaves, the colors being as true as can be reasonably done by conventional photographic procedures; and, FIG. 2, bud detail, leaf and branching habit, and petal translucency; and FIG. 3, the full growth habit of the plant (taken in Mid-October toward the end of the Gulf Coast growing season and showing some early fall foliage color).

DETAILED DESCRIPTION OF THE NEW PLANT

The following is a detailed description of the new variety, color terminology being in accordance with the Royal Horticultural Society Colour Chart (indicated by initials RHS-number) for the closest match, AND/OR with ordinary dictionary significance.

THE PLANT

Type: Root-hardy, herbaceous perennial.

Classification: Hybrid variety of Hibiscus, Section Muenchhusia (Fryxell, 1988).

Origin: Seedling.

Parentage: Is known to be a selection from the BOST$_x$® breeding population which was established by cross-pollination between (1) a breeding line derived from crossing the commercially available Hibiscus×"Southern Belle" and the species hibiscus *H. Laevis* "Houston", (2) a breeding line derived from crossing *H. laevis* "Houston" and the species hibiscus *H. coccineus,* and (3) a breeding line derived from crossing *H. coccineous* and Hibiscus "Southern Belle".

Propagation: Holds its distinguishing characteristics through succeeding propagations by cuttings and divisions.

Form: Bushy annual growth from perennial roots.

Habit: Upright and much branched.

Growth: Vigorous.

Foliage:

*Arrangement.*—Alternate.

*Size.*—Four to over twelve inches along primary vein, approximately as wide across lateral veins. Central lobe always larger than laterals.

*Margins.*—Serrate.

*Color.*—Top-deep green (RHS-146A/137A).* Underside — lighter green (RHS-147B/138B).*

*Veins.*—Top and bottom — pale green (RHS-147D).*

* Closest approximation. None of the RHS greens exactly match the foliage colors.

*Petiole.*—Length three to ten inches. Lenticels — none.

*Form.*—Three-parted (young) to five-parted (older); palmately lobed.

*Stipules.*—None.

Stem: Cane-like, pale blue-green (RHS-138D) when young; blushing to red in full sun and in the Fall. Basal cane diameter is approximately two to three inches.

*Height.*—Giant — 10 to 15 feet.

THE FLOWER

Blooming habit: Continuous and free blooming, June-November (or until frost).

Corolla:

*Diameter.*—eight to ten inches. The bloom is recurved, rather than flat, so the diameter is less than the sum of the length of two petals.

*Shape.*—Deeply flared, fully-open bell, with petals overlapping basally and separate distally.

Involucral bracts:

*Number.*—Twelve.

*Color.*—Medium green (RHS-144A).

Calyces:

*Number of sepals.*—Five, each 5-nerved.

*Shape.*—deeply dissected, arrow-shaped with apical point.

*Color.*—Pale green (RHS-144B).

Filaments:

*Color.*—Deep pink (RHS-55A).

Stamens: Numerous.

Stigma:

*Color.*—Pink (RHS — 55C) overlain with pale yellow setae.

*Number.*—Five, rounded, discoid, hairy.

Staminal column:

*Color.*—Pink (RHS-55C).

*Length.*—Two- to two-and-one-half inches. Upper two thirds antheriferous.

*Base of pistil or very center of throat.*—Color — White (RHS-155C).

*Pollen.*—Light yellow to buff (RHS-164B).

Petalage: Shape-Obovate, slightly assymetrical, apical point rotated to left of center (front side), recurved at base to form slight green star of revealed clayx.

*Size.*—Four-and-one-half to six inches (style to tip), depending on night temperatures and culture.

*Aspect.*—Central one-third satiny, outer two-thirds translucent.

*Texture.*—Moderately thick, like broadcloth fabric.

*Color.*—Center eye zone — RHS-45A. First interzone= reddish block (RHS-187A/B). Second interzone= RHS-45A. Outer petal=RHS-53A. Petal veins= RHS-53D.

The overall effect of the bloom is that of a hugh red star with four zones of red.

Flowers: Numerous, elegant; individual flowers last one day, two days in cooler weather.

Peduncle: Three to five inches; medium thickness; stiff.

GENERAL CHARACTERISTICS AND CULTURE

Blooming periods: Last May to November (or frost) on the Gulf Coast, July to frost in cooler zones. From the onset of the blooming period, the plant is seldom without flowers.

Hardiness: Root hardy to at least Zone 5 (farther North if well mulched). Dormancy is apparently triggered by soil temperatures rather than strictly by photoperiod..1m 0.

Breaking action: Very tough. Young stems bend, straighten and regrow, older stems remain upright.

Rooting: Excellent. Hormone unnecessary, especially under mist.

Growth regulator: Not required. Optional for holding in pots in commercial nurseries.

Shipping tolerance: Excellent, especially as liners or when dormant.

I claim:

1. A new and distinct cultivar of Hibiscus named 'Quatro Rojo', as shown and described.

* * * * *